United States Patent [19]

Lüthy et al.

[11] Patent Number: 5,262,386
[45] Date of Patent: Nov. 16, 1993

[54] PYRIMIDINYL- AND TRIAZINYL-SALICYLAMIDES AND THEIR USE AND PREPARATION

[75] Inventors: Christoph Lüthy, Schwerzenbach, Switzerland; Raymond Fisher, Hyde, England

[73] Assignee: Ciba-Geigy Corporation, Ardsley, N.Y.

[21] Appl. No.: 811,382

[22] Filed: Dec. 20, 1991

[30] Foreign Application Priority Data

Dec. 21, 1990 [GB] United Kingdom ............... 9027864

[51] Int. Cl.$^5$ ............... A01N 43/54; C07D 239/34; C07D 239/38; C07D 239/52
[52] U.S. Cl. ............... 504/242; 504/218; 504/219; 504/227; 504/243; 540/601; 544/243; 544/300; 544/301; 544/302; 544/303; 544/304; 544/306; 544/310; 544/311; 544/312; 544/313; 544/314; 544/316; 544/317; 544/318
[58] Field of Search ............... 544/300–304, 544/306, 310–314, 316–318, 243; 540/601; 504/242, 243

[56] References Cited

U.S. PATENT DOCUMENTS

| | | | |
|---|---|---|---|
| 5,015,285 | 5/1991 | Rheinheimer | 71/92 |
| 5,057,143 | 10/1991 | Rheinheimer | 71/92 |

FOREIGN PATENT DOCUMENTS

| | | |
|---|---|---|
| 0223406 | 5/1987 | European Pat. Off. |
| 0249707 | 12/1987 | European Pat. Off. |
| 0249708 | 12/1987 | European Pat. Off. |
| 0315889 | 5/1989 | European Pat. Off. |
| 0346789 | 12/1989 | European Pat. Off. |
| 0360163 | 3/1990 | European Pat. Off. |
| 0426476 | 5/1991 | European Pat. Off. |
| 0336494 | 10/1998 | European Pat. Off. |

*Primary Examiner*—Cecilia Tsang
*Attorney, Agent, or Firm*—Kevin T. Mansfield; Edward McC. Robert

[57] ABSTRACT

Pyrimidinyl- and triazinyl-salicylamides of the formula I

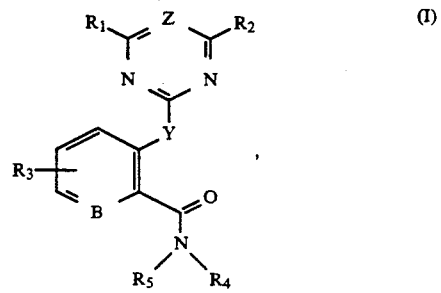

in which the meanings of the radicals are described in claim 1, and the salts of compounds of the formula I which have a free hydroxycarbonyl group have a herbicidal and plant-growth regulating action. They are suitable as active substances in weed killers and in compositions for positively influencing the growth of crop plants.

24 Claims, No Drawings

PYRIMIDINYL- AND TRIAZINYL-SALICYLAMIDES AND THEIR USE AND PREPARATION

The present invention relates to novel pyrimidinyl- and triazinyl-salicylamides which have a herbicidal action and are plant-growth-regulating, to processes for their preparation, to compositions containing them as active substances, and to their use for controlling weeds, especially selectively in crops, or for regulating and inhibiting plant growth.

It has been found that compounds of the formula (I) have a herbicidal and plant-growth-regulating action. They are therefore suitable as active substances in weed killers and in compositions for positively influencing the growth of crop plants.

The pyrimidinyl- and triazinyl-salicylamides according to the invention are those of the formula I

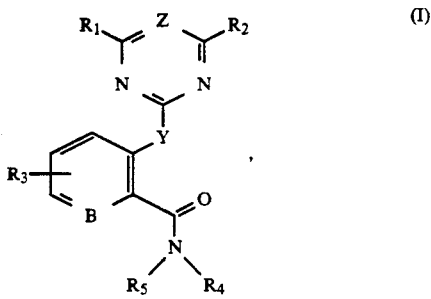

in which B is nitrogen, methine, or fluorine-, chlorine-, methyl-, methoxy-, 2-propenyloxy-, 2-propynyloxy-, difluoromethoxy-, phenoxy-, methylthio-, phenylthio-, phenyl- or benzyloxy-substituted methine; Y is oxygen or sulfur; Z is methine or nitrogen; $R_1$ is chlorine, methyl, methoxy, ethoxy, difluoromethoxy, methylamino, ethylamino or dimethylamino; $R_2$ is methyl, methoxy or difluoromethoxy; $R_3$ is hydrogen, fluorine, chlorine, methyl or methoxy; $R_4$ is one of the groups (a), (b) or (c)

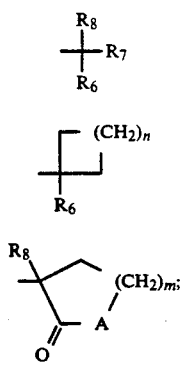

$R_5$ is hydrogen, methyl, or together with $R_7$ is —(CH$_2$)$_p$—, —CH$_2$SCH$_2$— or —CH$_2$CHOHCH$_2$—; $R_6$ is hydroxymethyl, formyl, cyano, hydroxyimino, $C_{1-4}$-alkoxyimino, phosphono, phosphino, methylphosphino or a group COX; $R_7$ is hydrogen; $C_{1-4}$alkyl which is unsubstituted or substituted by hydroxyl, $C_{1-4}$alkoxy, mercapto, acylmercapto, $C_{1-4}$-alkylthio, vinyl, phenyl, 4-hydroxyphenyl, 4-imidazolyl, 3-indolyl, hydroxycarbonyl, $C_{1-4}$alkoxycarbonyl, 2-propenyloxycarbonyl, cyano, carbamoyl; trifluoromethyl; ethynyl; vinyl which is unsubstituted or substituted by chlorine or methoxy; or phenyl which is unsubstituted or substituted by fluorine, chlorine, methyl, trifluoromethyl or methoxy; or cyano or $C_{1-4}$-alkoxycarbonyl; $R_8$ is hydrogen or methyl; A is oxygen, sulfur or —NH—; m is 1, 2 or 3; n is 0, 1, 2 or 3; p is 2 or 3; X is hydroxyl, $C_{1-4}$alkoxy, $C_{3-4}$alkenyloxy, mercapto, $C_{1-4}$alkylthio, amino, $C_{1-4}$alkylamino, $C_{2-4}$dialkylamino, or $C_{1-4}$-alkoxy, $C_{3-4}$-alkenyloxy, mercapto, $C_{1-4}$-alkylthio, amino, $C_{1-4}$-alkylamino, $C_{2-4}$dialkylamino, $C_{1-4}$-alkoxyamino substituted by phenyl, benzyloxy or $C_{1-2}$-alkoxy, or a further one of the groups (d), (e) or (f)

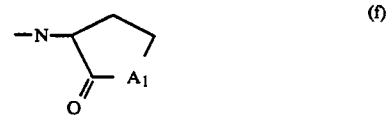

$R_9$ is hydrogen, $C_{1-4}$alkyl or benzyl; $R_{10}$ is hydroxymethyl, cyano or a group COQ'; Q is hydroxyl, $C_{1-4}$alkoxy, 2-propenyloxy, benzyloxy, amino or a group (d); Q' is hydroxyl, $C_{1-4}$alkoxy, 2-propenyloxy, benzyloxy, amino or a group (d); and the salts of those compounds of the formula I which have a free hydroxycarbonyl group.

The alkyl and alkenyl radicals in formula I can be straight-chain or branched. This is also true for the, or each, alkyl moiety of alkoxy-, alkylthio-, alkoxycarbonyl- and of further alkyl-containing groups.

If the compounds of the formula I contain an asymmetric carbon atom, this results in the fact that the compounds can occur in optically isomeric forms. If there is an aliphatic C=C double bond, geometric isomerism can also occur. The formula I therefore also embraces all stereoisomers which are possible and which are in the form of enantiomers, diastereomers or their mixtures. Some compounds of the formula I can occur in tautomeric forms (for example keto-enol or imine-enamine tautomerism). The formula I therefore also embraces all tautomers.

Preferred compounds of the formula I are those in which a) B is methine, preferably substituted by fluorine or chlorine; or oxygen;
b) Y is oxygen;
c) Z is methine;
d) $R_1$ and $R_2$ are methoxy;
e) $R_3$ is hydrogen;
f) $R_4$ is a group (a);
g) $R_5$ is hydrogen;
h) $R_6$ is cyano or a COX group;
i) $R_7$ is hydrogen, $C_{1-4}$alkyl, 2-propenyl or together with $R_5$ is —CH$_2$CH$_2$CH$_2$— or —CH$_2$SCH$_2$—;
j) $R_8$ is hydrogen; and
k) $R_4$ is a chiral group of the formula IA

(IA)

with <S> chirality.

Preferred compounds from the sub-group h) are those in which X is $C_{1-4}$alkoxy or amino.

Another preferred subgroup is formed by those compounds of the formula I in which $R_4$ is a group (c), A is oxygen or sulfur and m is 1, compounds in which $R_4$ is a group of the formula IF

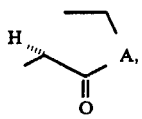
(IF)

with <S> chirality being very particularly preferred.

A group of compounds of the formula I which excels because of its good biological activity is those in which
$R^1$ is methoxy, ethoxy or difluoromethoxy;
$R^2$ is methoxy;
$R^3$ is hydrogen;
B is nitrogen, methine or chlorine- or fluorine-substituted methine;
Y is oxygen or sulfur;
Z is methine or nitrogen; and in which
$NR^4R^5$ has one of the meanings given in Table 1:

TABLE 1

Q1: 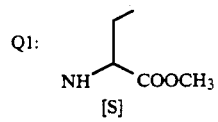

Q2: 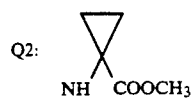

Q3: 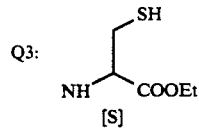

Q4: 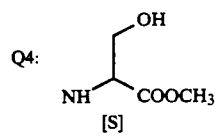

Q5: 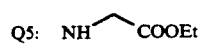

Q6: 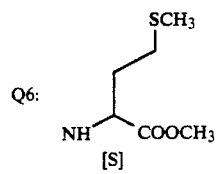

TABLE 1-continued

Q7: 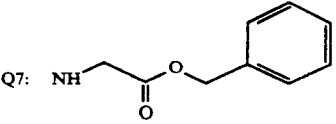

Q8: 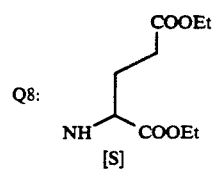

Q9: 

Q10: 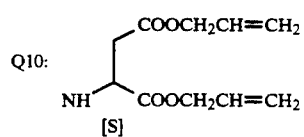

Q11: 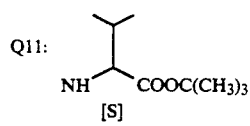

Q12: 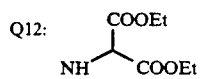

Q13: 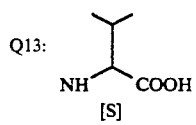

Q14: 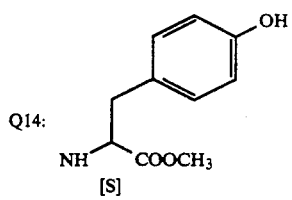

Q15: 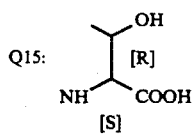

Q16: 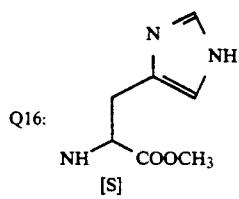

TABLE 1-continued
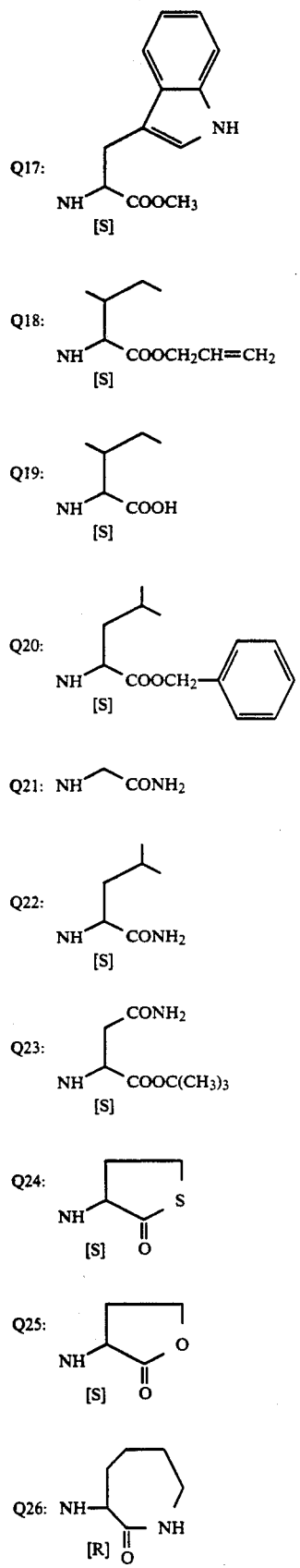
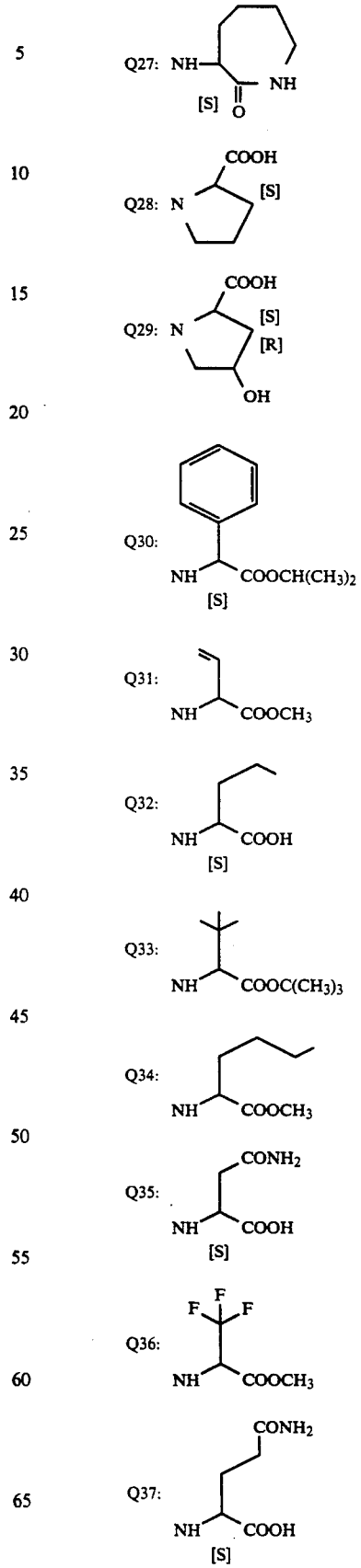

TABLE 1-continued
Q38: 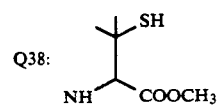
Q39: 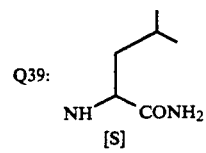
Q40: 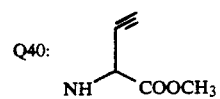
Q41: 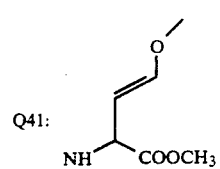
Q42: 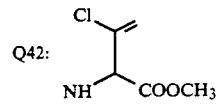
Q43: 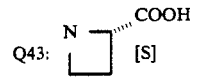
Q44: 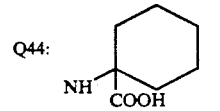
Q45: 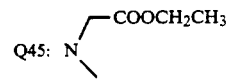
Q46: 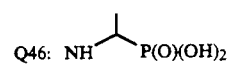
Q47: 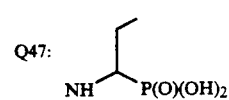
Q48: 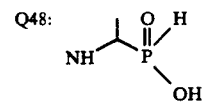
Q49: 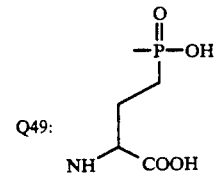
TABLE 1-continued
Q50: 
Q51: 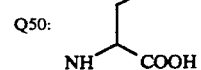
Q52: 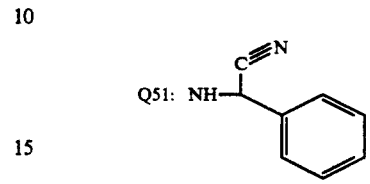
Q53: 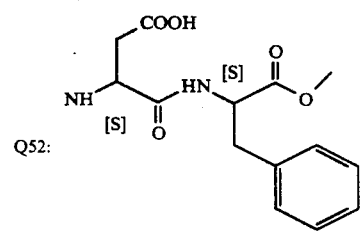
Q54: 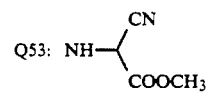
Q55: 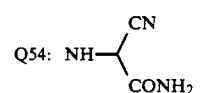
Q56: 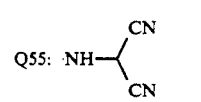
Q57: 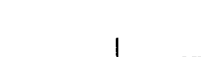
Q58: 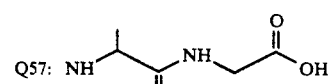
Q59: 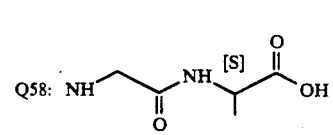
Q60: 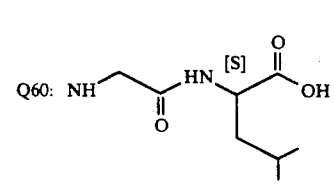

TABLE 1-continued

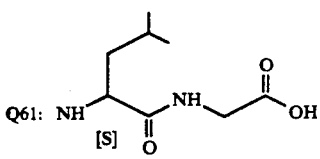

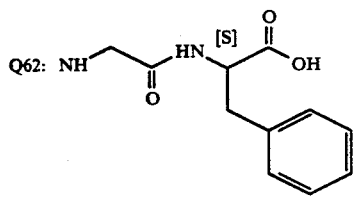

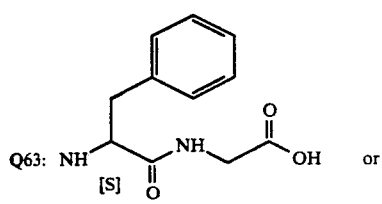

or

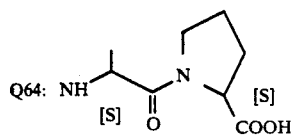

Preferred individual compounds from the scope of the formula I to be mentioned are:
methyl N-(o)-((4,6-dimethoxy-2-pyrimidinyl)oxy)benzoyl)glycinate (Examples 1 and 2);
ethyl N-(o-((4,6-dimethoxy-2-pyrimidinyl)oxy)benzoyl)-L-alaninate (Example 20);
rac-o-((4,6-dimethoxy-2-pyrimidinyl)oxy)-N-(dihydro-2-oxo-3(2H)-thienyl)benzamide (Example 5);
methyl N-(o-((4,6-dimethoxy-2-pyrimidinyl)oxy)benzoyl)-L-alaninate (Example 21);
methyl N-(o-((4,6-dimethoxy-2-pyrimidinyl)oxy)benzoyl)-L-valinate (Example 22);
methyl N-(o-((4,6-dimethoxy-2-pyrimidinyl)oxy)benzoyl)-L-leucinate (Example 23);
rac-N-(1-carbamoyl-1,2-dimethylpropyl)-o-((4,6-dimethoxy-2-pyrimidinyl)thio)benzamide (Example 7);
tert-butyl 1-(o-((4,6-dimethoxy-2-pyrimidinyl)oxy)benzoyl)-L-prolinate (Example 26);
methyl N-((3-((4,6-dimethoxy-2-pyrimidinyl)oxy)-2-pyridyl)carbonyl)-L-alaninate (Example 27);
methyl N-((3-((4,6-dimethoxy-2-pyrimidinyl)oxy)-2-pyridyl)carbonyl)glycinate (Example 9);
o-((4,6-dimethoxy-2-pyrimidinyl)oxy)-N-(<S>-1-(hydroxymethyl)-2-methylpropyl)benzamide (Example 11); and
N-(1-cyano-1-methylethyl)-o-((4,6-dimethoxy-2-pyrimidinyl)oxy)benzamide (Example 13).

The novel compounds of the formula I can be prepared by reacting a compound of the formula II

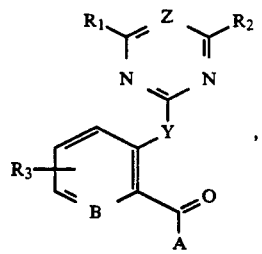

in which A is a leaving group, preferably chlorine, or imidazolyl; or an acid anhydride of the formula II'

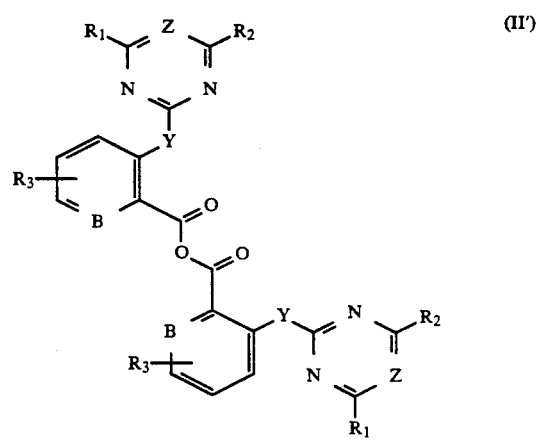

with an amine of the formula III

The reaction is advantageously carried out in the presence of a base. Suitable bases are tertiary amines, for example triethylamine, N,N-dimethylaniline or 2,5-dimethylpyridine. The reaction is preferably carried out in the presence of a solvent. Suitable solvents are:
hydrocarbons, for example toluene;
halogenated hydrocarbons, for example dichloromethane, 1,2-dichloroethane or chlorobenzene;
ethers, for example diethyl ether, dimethoxyethane or tert-butyl methyl ether;
aprotic solvents, for example acetonitrile;
protic solvents, for example alcohols, in particular ethanol, or water; or
two-phase systems, for example a mixture of dichloromethane and water, toluene and water, or diethyl ether and water.

Furthermore, the novel compounds of the formula I can be prepared by reacting a compound of the formula V

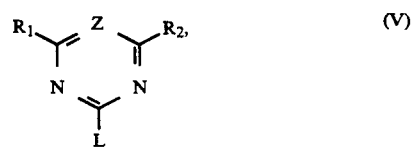

in which L is a leaving group, in particular halogen or substituted or unsubstituted alkylsulfonyl, benzylsulfonyl, phenylsulfonyl, alkylsulfonyloxy, benzylsulfonyloxy, phenylsulfonyloxy, or 3-alkylsulfonyl-1H-1,2,4-triazol-1-yl, for example 3-methylsulfonyl-1H-1,2,4-triazol-1-yl, and preferably chlorine, methanesulfonyl, ethanesulfonyl or benzylsulfonyl, with salicylamide derivative of the formula VII

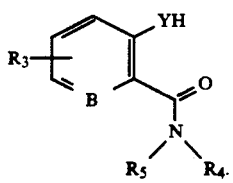
(VII)

The reaction is advantageously carried out in the presence of an inert diluent, in particular of an organic, advantageously aprotic, solvent, and preferably an aliphatic or cyclic ether, for example dimethoxyethane or tetrahydrofuran;

an aliphatic ketone, for example acetone or 2-butanone;

an aliphatic nitrile, for example acetonitrile or propionitrile;

dimethylformamide;

N-methylpyrrolidone; or a heteroaromatic compound, for example pyridine or lutidine;

a base, in particular an alkali metal hydride, for example sodium hydride or potassium hydride;

an alkaline earth metal hydride, for example calcium hydride;

an alkali metal hydrogen carbonate, for example sodium hydrogen carbonate, or potassium hydrogen carbonate;

an alkali metal carbonate, for example sodium carbonate or potassium carbonate;

an alkaline earth metal carbonate, for example calcium carbonate or magnesium carbonate;

an aliphatic tertiary amine, for example triethylamine;

a completely substituted amidine, for example diazabicycloundecene; or a basic heteroaromatic compound, for example pyridine;

a reaction-accelerating additive, in particular a crown ether;

a phase-catalyst;

a compound which temporarily replaces the leaving group L, preferably dimethylaminopyridine; or a compound which, in the event that L is halogen, activates the leaving group, preferably a silver or copper salt, for example silver nitrate or copper(I) chloride.

The reaction is carried out in the temperature range between 0° C. and 160° C., in particular between 20° C. and 100° C., preferably between 20° C. and the boiling point of the reaction mixture.

Compounds of the formula II in which A is chlorine can be prepared, for example, by reacting an acid of the formula IV

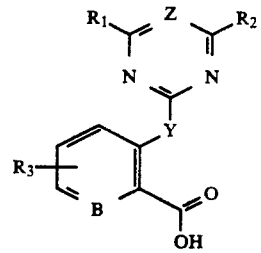
(IV)

with a chlorinating agent such as phosphorus oxychloride, thionyl chloride, oxalyl chloride or phosgene, preferably phosphorus oxychloride, in the presence of an auxiliary base, for example triethylamine, dimethylaniline or pyridine, and, if desired, in the presence of a solvent such as a hydrocarbon, for example toluene; a chlorohydrocarbon, for example methylene chloride; an ether, for example tetrahydrofuran, at a temperature from $-20°$ C. to the reflux temperature of the reflux mixture, preferably from $-5°$ C. to room temperature.

However, it is not necessary to isolate the intermediate of the formula II, i.e. in the present case the acid chloride. The latter is advantageously reacted directly "in situ" with the amine of the formula III, if desired in the presence of an additional base such as triethylamine. This reaction is likewise carried out in a temperature range from about $-20°$ C. to the reflux temperature of the solvent used, preferably between $-5°$ C. and room temperature.

On the other hand, it is advantageous to start with an acid anhydride of the formula II'. These acid anhydrides are novel compounds and therefore likewise form a subject of the present invention. The novel pyrimidinyl- and triazinyl-salicylic anhydrides are those of the formula II'

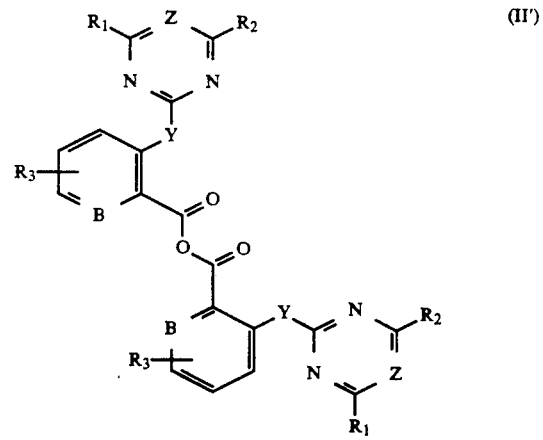
(II')

in which B is nitrogen, methine, or fluorine-, chlorine-, methyl-, methoxy-, 2-propenyloxy-, 2-propynyloxy-, difluoromethoxy- or benzyloxy-substituted methine; Y is oxygen or sulfur; Z is methine or nitrogen; $R_1$ is chlorine, methyl, methoxy, ethoxy, difluoromethoxy, methylamino, ethylamino or dimethylamino; $R_2$ is methyl, methoxy or difluoromethoxy; and $R_3$ is hydrogen, fluorine, chlorine, methyl or methoxy.

Preferred compounds of the formula II' are those in which a) B is methine or nitrogen;

b) Y is oxygen;

c) Z is methine;
d) $R_1$ and $R_2$ are methoxy; and
f) $R_3$ is hydrogen.

The compounds of the formula II' can be prepared by treating an acid of the formula (IV)

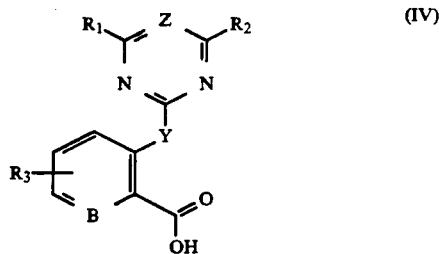

with phosphorus oxychloride and triethylamine. It is preferred in this context to use 0.50 to 0.55 equivalent of phosphorus oxychloride and 2.0 to 3.0 equivalents of triethylamine per equivalent of the acid of the formula IV.

Acids of the formula IV are either previously known (for example from EP-A1 0,223,406, 0,249,707, 0,249,708, 0,287,079, 0,315,889, 0,336,494 and 0,346,789), or they can be prepared by the known processes, for example by condensing a compound of the formula V in which the substituents have the above-mentioned meaning, but L is preferably chlorine, methanesulfonyl, ethanesulfonyl or benzylsulfonyl, with a salicylic acid derivative of the formula VI

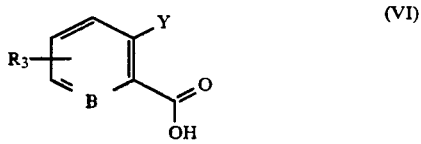

in the presence of a suitable base such as potassium carbonate, potassium hydroxide or sodium hydride, and in the presence of a suitable solvent such as acetone, methyl ethyl ketone, acetonitrile, dimethylformamide or dimethyl sulfoxide, advantageously in a temperature range from 0° C. to reflux temperature, but preferably between 10° C. and 60° C.

Compounds of the formulae III, V, VI and VII are either previously known or they can be prepared by the processes known per se from the literature.

The compounds of the formula I (hereinafter also called "active substances") have herbicidal properties and are suitable for controlling weeds including grass weeds, for example, inter alia, Agropyron repens, Alopecurus myosuroides, Avena fatua, Bromus inermis, Echinochloa crus-galli, Poa annua, Sorghum halepense, Abutilon theophrasti, Amaranthus retroflexus, Cassia obtusifolia, Chenopodium album, Galium aparine, Matricaria chamomilla, Sinapis arvensis and Stellaria media in various crops, for example, inter alia, rice crops, in particular paddy rice, wheat, maize, soya, oilseed rape, sunflower and cotton. Moreover, the compounds are pre-emergence and post-emergence herbicides. In some representatives of the compounds of the formula I, a good selectivity was noticed, for example in the control of weeds in soya crops and cotton crops.

Furthermore, the compounds of the formula I have plant-growth-regulating properties and are suitable as active substances for positively influencing the growth of crop plants. This effect can lead to a desired growth inhibition in crop plants as well as sufficiently inhibit the germination of weeds so as to eliminate them as competitors of the crop plants. With regard to ecological interactions, this is advantageous and hence extremely desirable. Factors which must be mentioned in particular are the protection of the soil surface against desiccation and/or erosion and the reduction of the bulk of weed seeds in the soil (while simultaneously preventing flowering and the formation of more seeds). Under given circumstances, this action is to be preferred to the complete prevention of weed formation, which may be limited to a period of time.

In practice, a concentration from 1 g to 3 kg of the compound of the formula I per ha, preferably from 10 g to 1 kg/ha, is usually sufficient to achieve the desired herbicidal effect. To achieve the desired herbicidal effect combined with an optimum tolerance by crop plants, the range from 10 to 100 g/ha as a pre-emergence treatment and from 100 to 1000 g/ha as a post-emergence treatment are particularly favourable.

The weed killers and plant-growth-regulating compositions according to the invention contain an effective amount of at least one compound of the formula I and, as a rule, also formulation auxiliaries. Advantageously, they contain at least one formulation auxiliary from each of the following groups:
solid carriers;
solvents or dispersing agents;
surfactants (wetting agents and emulsifiers);
dispersants (without surfactant action); and
stabilisers.

As a rule, the pesticidal preparations contain, besides the active substances of the formula I, 1 to 99% of a formulation auxiliary from the group comprising
solid carriers;
solvents or dispersing agents;
dispersants (without surfactant action); and
stabilisers; and 0 to 25%, in particular 0.1 to 25%, of a
surfactant (wetting agent and emulsifiers).

Using auxiliaries of these types and others, the compounds of the formula I, i.e. the herbicidal active substances, can be converted into the customary formulations, such as dusts, powders, granules, solutions, emulsions, suspensions, emulsifiable concentrates, pastes and the like.

In general, the compounds of the formula I are water-insoluble and can be formulated following methods customary for water-insoluble compounds, using the known formulation auxiliaries. The compositions can be prepared in a manner known per se, for example by mixing the particular active substance with solid carriers, by dissolving or suspending in suitable solvents or dispersing agents, if desired with the use of surfactants as wetting agents or emulsifiers and/or dispersants, or by diluting of already prepared emulsifiable concentrates with solvents or dispersing agents.

The following are mainly suitable as solid carriers:
natural minerals, such as chalk, dolomite, limestone, clays and silica and their salts, for example kieselguhr, kaolin, bentonite, talc, attapulgite or montmorillonite;
synthetic minerals such as highly disperse silica, alumina or silicates;
organic substances such as cellulose, starch, urea or synthetic resins; and
fertilisers such as phosphates or nitrates.

Such carriers can be, for example, in the form of powders or granules.

The following are mainly suitable as solvents or dispersing agents:

aromatic substances such as benzene, toluene, xylene and alkylnaphthalenes;

chlorinated aromatic substances and chlorinated aliphatic hydrocarbons such as chlorobenzene, chloroethylenes or methylene chloride;

aliphatic hydrocarbons such as cyclohexane or paraffins, for example mineral oil fractions;

alcohols such as butanol or glycol and their ethers and esters;

ketones such as acetone, methyl ethyl ketone, methyl isobutyl ketone or cyclohexanone; and strongly polar solvents or dispersing agents, such as dimethylformamide, N-methylpyrrolidone or dimethyl sulfoxide (solvents of these types preferably having flashpoints of at least 30° C. and boiling points of at least 50° C.), or water.

Other suitable solvents or dispersing agents are also so-called liquefied gaseous extenders or carriers, which are products which are gaseous at room temperature and under atmospheric pressure. Examples of such products are, in particular, aerosol propellants such as halohydrocarbons, for example dichlorodifluoromethane.

If the weed killer according to the invention is in the form of a pressurised-gas pack, it is advantageous to employ a solvent in addition to the propellant.

The surfactants (wetting agents and emulsifiers) can be non-ionic compounds such as:

condensation products of fatty acids, fatty alcohols or fat-substituted phenols with ethylene oxide;

fatty acid esters and fatty acid ethers of sugars or polyhydric alcohols;

the products which are obtained from sugars or polyhydric alcohols by condensation with ethylene oxide;

block polymers of ethylene oxide and propylene oxide; or alkyldimethylamine oxides.

The surfactants can also be anionic compounds such as:

soaps;

fatty sulfate esters, for example sodium dodecyl sulfate, sodium octadecyl sulfate or sodium cetyl sulfat;

alkylsulfonates, arylsulfonates or fatty aromatic sulfonates, such as alkylbenzenesulfonates, for example calcium dodecylbenzenesulfonate or butylnaphthalenesulfonates; or more complex fatty sulfonates, for example the amide condensation products of oleic acid and N-methyltaurine, or the sodium sulfonate of dioctyl succinate.

Finally, the surfactants can be cationic compounds such as alkyldimethylbenzylammonium chlorides, dialkyldimethylammonium chlorides, alkylmethylammonium chlorides or ethoxylated ammonium chlorides.

Suitable dispersants (without surfactant action) are mainly the following: lignin, sodium salts and ammonium salts of ligninsulfonic acids, sodium salts of maleic anhydride/diisobutylene copolymers, sodium salts and ammonium salts of sulfonated polycondensation products from naphthalene and formaldehyde, or sulfite waste liquors.

Examples which can be employed as dispersants which are particularly suitable as thickeners or sedimentation inhibitors are methylcellulose, carboxymethylcellulose, hydroxyethylcellulose, polyvinyl alcohol, alginates, caseinates or blood albumin.

Examples of suitable stabilisers are:

acid-binding agents, for example epichlorohydrin, phenyl glycidyl ethers or soya epoxides;

antioxidants, for example gallic esters or butylhydroxytoluene;

UV absorbers, for example substituted benzophenones, diphenylacrylonitrilic esters or cinnamic esters; or deactivators, for example salts of ethylenediaminotetraacetic acid, or polyglycols.

The weed killers and plant-growth-regulating compositions according to the invention can also contain further active substances in addition to the compounds of the formula I, for example insecticides, acaricides, nematicides, molluscicides, bactericides fungicides, herbicides, plant growth regulators, fertilisers and trace element sources. Such combined compositions are suitable for broadening the spectrum of action.

In general, the weed killers according to the invention contain between 0.001 and 95 percent by weight, preferably between 0.5 and 75 percent by weight, of one or more of the compounds of the formula I as active substance. For example, they can be present in a form which is suitable for storage and transport. In such formulations, for example emulsifiable concentrates, the concentration of active substance is generally in a higher range, preferably between 1 and 50 percent by weight, in particular between 5 and 30 percent by weight. Using identical or different inert substances, for example, these formulations can be diluted down to the concentration of active substance which is suitable for use in practice, i.e. preferably about 0.001 to 10 percent by weight, in particular about 0.005 to 5 percent by weight. However, the concentrations of active substance can be lower or higher.

As mentioned, the weed killers according to the invention can be prepared in a manner known per se.

To prepare preparations in the form of powders, the active substance, i.e. at least one compound of the formula I, can be mixed with a solid carrier, for example by grinding them together. Alternatively, the solid carrier can be impregnated with a solution or suspension of the active substance, and the solvent or dispersing agent is then removed by evaporation, heating or filtering off under reduced pressure. Such compositions in the form of powders can be rendered readily wettable with water by adding surfactants or dispersants, so that they can be converted into aqueous suspensions which are suitable, for example, as compositions for spraying.

The active substance can also be mixed with the surfactant and a solid carrier to form a wettable powder which is dispersible in water, or it can be mixed with a solid, pregranulated carrier to form a product in the form of granules.

If desired, the active substance can be dissolved in a solvent which is not miscible with water, for example a higher-boiling hydrocarbon. The latter expediently contains dissolved emulsifier, so that the solution is self-emulsifying when it is added to water. On the other hand, the active substance can be mixed with an emulsifier, and the mixture can then be diluted with water to the desired concentration. Moreover, the active substance can be dissolved in a solvent and the solution then be mixed with an emulsifier. Such a mixture can likewise be diluted with water to the desired concentration. In this manner, emulsifiable concentrates or ready-to-use emulsions are obtained.

The weed killers described can be used according to the invention following customary application methods such as spraying, atomising, dusting, pouring or broadcasting.

The following examples are intended to illustrate the invention in greater detail.

A. PREPARATION OF COMPOUNDS OF THE FORMULA I

EXAMPLE 1

Methyl N-(o-((4,6-dimethoxy-2-pyrimidinyl)oxy)benzoyl)glycinate 12.6 g of o-((4,6-dimethoxy-2-pyrimidinyl)oxy)benzoic acid are dissolved in 500 ml of dichloromethane, and the solution is treated with 30 g of triethylamine. 7.5 g of phosphorus oxychloride, dissolved in 25 ml of dichloromethane, are added dropwise at −5° C., and stirring is continued for 5 minutes. A solution of 8.9 g of freshly prepared methyl glycinate in 100 ml of water is then added with vigorous stirring. The mixture is allowed to come to room temperature in the course of 15 minutes, while stirring is continued. The organic phase is then separated off, washed three times using fresh water, dried over magnesium sulfate and evaporated. The residue which remains is purified by means of flash chromatography. Pure methyl N-o-((4,6-dimethoxy-2-pyrimidinyl)oxy)benzoyl)glycinate is obtained as a virtually colourless oil; $^1$H-NMR (CDCl3): 3.61, s, COOCH$_3$, 3.81, s, twice OCH$_3$, 4.16, d, J=5 Hz, CH$_2$, 5.82, s, —CH=, 7.22–8.06, NH and 4 aromatic H atoms.

EXAMPLE 2

Methyl N-o-((4,6-dimethoxy-2-pyrimidinyl)oxy)benzoyl)glycinate 5.35 g of bis-o-((4,6-dimethoxy-2-pyrimidinyl)oxy)-benzoic anhydride and 2 g of triethylamine are initially introduced into 100 ml of dichloromethane. A freshly prepared solution of 1.78 g of methyl glycinate in 15 ml of water is added while stirring, and stirring is continued for 1 hour at room temperature. The organic phase is separated off, washed with sodium hydrogen carbonate solution and water, dried and evaporated. In this manner, 3.5 g of virtually pure product are obtained which, according to TLC, is identical with the methyl N-(o-((4,6-dimethoxy-2-pyrimidinyl)oxy)benzoyl)glycinate prepared in Example 1 (TCL mobile phase: ethyl acetate/hexane 2:1, R$_f$ value: 0.55).

EXAMPLE 3

N-o-((4,6-Dimethoxy-2-pyrimidinyl)oxy)benzoyl)-L-alanine 6.0 g of tert-butyl N-(o-((4,6-dimethoxy-2-pyrimidinyl)oxy)benzoyl)-L-alaninate (Example 31) are dissolved in 40 ml of trifluoroacetic acid, and the solution is kept in the sealed reaction vessel for 2 days at room temperature. The readily volatile components are then evaporated on a rotary evaporator. The oily residue which remains is taken up in dichloromethane and washed twice using 300 ml of water. The mixture is dried over sodium sulfate and evaporated. For further purification, the oil which remains is purified by means of gradient flash chromatography. The gum-like residue of 4.8 g is pure N-(o-((4,6-dimethoxy-2-pyrimidinyl)oxy)benzoyl)-L-alanine: R$_f$: 0.19 (ethyl acetate/methanol 3:1).

EXAMPLE 3a

N-(o-((4,6-Dimethoxy-2-pyrimidinyl)oxy)benzoyl)-(L-Leu)-L-Ala) ethyl ester 3.7 g of N-(o-((4,6-dimethoxy-2-pyrimidinyl)oxy)benzoyl)-L-leucine (Example 34) are taken up in 250 ml of dichloromethane, treated in succession with 3.3 g of ethyl L-alaninate hydrochloride and 7.5 g of triethylamine, and the stirred mixture is cooled to −5° C. At this temperature, a solution of 1.6 g of phosphorus oxychloride in 5 ml of dichloromethane is added dropwise and the mixture is subsequently stirred for 20 minutes. The organic phase is then washed three times with 250 ml of water, dried over sodium sulfate and evaporated. The product which remains is purified by means of gradient flash chromatography. Pure N-(o-((4,6-dimethoxy-2-pyrimidinyl)oxy)benzoyl)(L-Leu)-(L-Ala) ethyl ester is obtained as a glassy product; R$_f$: 0.36 (ethyl acetate/hexane 2:1).

EXAMPLE 3b

N-(o-((4,6-Dimethoxy-2-pyrimidinyl)oxy)benzoyl)-(L-Phe)-(L-Ala) ethyl ester

In the same manner, the N-(o-((4,6-dimethoxy-2-pyrimidinyl)oxy)benzoyl)-(L-phe)-(L-Ala) ethyl ester is obtained as a glassy product from N-(o-((4,6-dimethoxy-2-pyrimidinyl)oxy)benzoyl)-L-phenylalanine (Example 35) and ethyl L-alaninate hydrochloride; R$_f$: 0.48 (ethyl acetate/hexane 2:1).

B. PREPARATION OF THE INTERMEDIATES OF THE FORMULA II

EXAMPLE 3c

Bis-o-((4,6-dimethoxy-2-pyrimidinyl)oxy)benzoic anhydride 27.6 g of bis-o-((4,6-dimethoxy-2-pyrimidinyl)oxy)-benzoic acid are introduced into a solution of 25 g of triethylamine in 500 ml of dichloromethane. The solution is cooled to −5° C., and then treated with a solution of 8 g of phosphorus oxychloride in 25 ml of dichloromethane, at this temperature. Stirring is continued for 10 minutes, and the solution is then briefly washed twice with 500 ml of ice-water in each case. The organic phase is dried and evaporated. Recrystallisation with ethyl acetate/hexane (7:8) gives 24.2 g of pure bis-o-((4,6-dimethoxy-2-pyrimidinyl)oxy)benzoic anhydride, m.p.: 120°–122° C.

The compounds of the formulae IB, IC, ID and IE which are listed in Tables 2 to 5 are prepared analogously to Examples 1 to 3.

The R$_f$ values were determined in ethyl acetate/hexane, unless otherwise specified.

TABLE 2

Compounds of the formula IB:

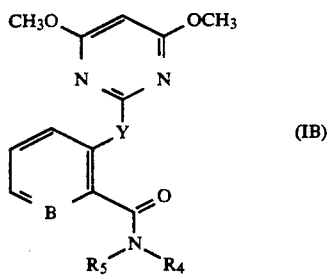

(IB)

| Ex. | Y | B | $R_5$ | $R_4$ | M.p. (°C.) | Phys. Data |
|---|---|---|---|---|---|---|
| 4 | O | C—H | H | ![](methyl isobutyrate ester) (rac) | 94–96 | |
| 5 | O | C—H | H | 3-methyl-tetrahydrothiophen-2-one (rac) | 74–78 | |
| 6 | O | C—H | H | isopropyl-CN (rac) | 126–128 | |
| 7 | S | C—H | H | isopropyl-C(CH3)-C(O)NH2 (rac) | 141–143 | |
| 8 | S | C—H | H | CH$_2$COOCH$_3$ | liquid | R$_f$: 0.50 (2:1) |
| 9 | O | N | H | CH$_2$COOCH$_3$ | 116–118 | |
| 10 | O | N | H | C(CH$_3$)$_2$COO— | 139–141 | |
| 11 | O | C—H | H | CH(iPr)CH$_2$OH <S> | liquid | R$_f$: 0.28 (2:1) |
| 12 | O | C—H | H | C(CH$_3$)$_2$CH$_2$OH | 88–89 | |
| 13 | O | C—H | H | CH$_2$C≡N | 157–159 | |
| 14 | O | C—H | H | C(CH$_3$)$_2$C≡N | 122–124 | |
| 15 | O | N | H | CH(CH$_3$)COOCH$_3$ <R> | solid | |
| 16 | O | N | H | C(CH$_3$)$_2$C(O)NH$_2$ with iPr (rac) | 188–189 | |

TABLE 2-continued
Compounds of the formula IB:
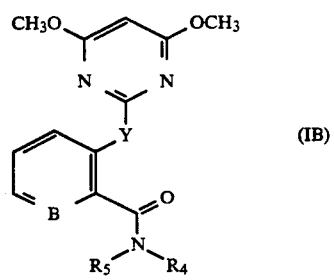
(IB)
| Ex. | Y | B | R₅ | R₄ | M.p. (°C.) | Phys. Data |
|---|---|---|---|---|---|---|
| 17 | O | C—H | H | ![S-acetyl methyl ester branched] (rac) | liquid | |
| 18 | O | N | H | ![thiolactone] (rac) | 124–125 | |
| 19 | O | C—H | H | $CH_2COOC(CH_3)_3$ | 116–117 | |
| 19.1 | O | C—H | H | ![lactone] (rac) | 109–111 | |
| 19.2 | O | C—H | H | CH(COOCH₂CH₃)₂ (rac) | | Rf: 0,59 (2:1) |
| 19.3 | O | C—H | H | ![lactam] <S> | 162–164 | |
| 19.4 | O | C—H | H | ![thioester ethyl] <S> | 71–75 | $[α]_D = +1,31°$ |
| 19.5 | O | C—H | H | ![thiolactone] <R> | 62–67 | |
| 19.6 | O | C—H | H | $C(CH_3)_2CON(CH_3)_2$ | 124–126 | |
| 19.7 | O | C—H | CH₃ | $C(CH_3)_2CONH_2$ | 123–124 | |
| 19.8 | O | C—H | H | ![allyl COOCH3 branched] (rac) | 105–109 | |

TABLE 2-continued

Compounds of the formula IB:

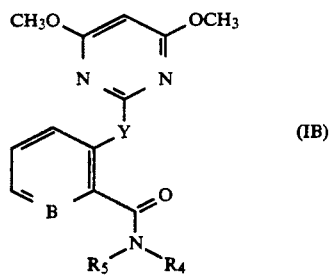

(IB)

| Ex. | Y | B | R₅ | R₄ | M.p. (°C.) | Phys. Data |
|---|---|---|---|---|---|---|
| 19.9 | O | C—H | H | ![CH(CH₃)CH₂OH] <S> | | Rf: 0,44/EtOAc) |
| 19.10 | O | C—H | H | ![CH₂C(=O)O-CH(Ph)CH₂OCH₃] <R> | | Rf: 0,24 (7:8) |
| 19.11 | O | N | H | C(CH₃)₂C≡N | 128–129 | |
| 19.12 | O | N | H | CH₂COOC(CH₃)₃ | 146–148 | |
| 19.13 | O | N | H | CH₂COOH | 194–195 | |
| 19.14 | O | N | H | ![CH(CH₃)CH₂OH] <S> | | Rf: 0,21 (EtOAc) |
| 19.15 | O | N | | —CH₂—SCH₂CH(COOCH₃)— (rac) | | Rf: 0,18 (2:1) |
| 19.16 | O | C—H | H | ![CH(CH₃)CHO] <S> | | Rf: 0,29 (2:1) |
| 19.17 | S | C—H | H | C(CH₃)₂CON(CH₃)₂ | 122–124 | |
| 19.18 | O | C—H | H | ![CH(CH₃)CH=N-OCH₃] <S> | | Rf: 0,54 (2:1) |
| 19.19 | S | C—H | H | C(CH₃)₂C≡N | | Rf: 0,48 (2:1) |
| 19.20 | O | N | H | ![γ-butyrolactone-3-yl] (rac) | | Rf: 0,40 (EtOAc) |
| 19.21 | O | C—H | H | ![lactone group] <S> | | Rf: 0,24 (2:1) |
| 19.22 | O | N | H | ![lactone group] <S> | | Rf: 0,40 (EtOAc) |

TABLE 2-continued
Compounds of the formula IB:
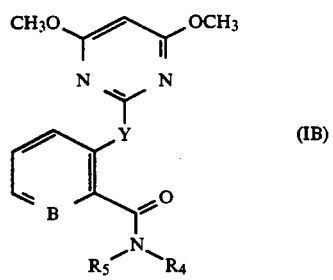
(IB)
| Ex. | Y | B | R5 | R4 | M.p. (°C.) | Phys. Data |
|---|---|---|---|---|---|---|
| 19.23 | O | C—H | H | cyclopropyl-COOCH3 | 119–120 | |
| 19.24 | O | C—H | H | cycloheptyl-COOCH3 | | Rf: 0,56 (2:1) |
| 19.25 | O | N | H | —CH2CH2—S—C(=O)—Et  \<S\> | 116–118 | |
| 19.26 | O | C—F | H | —CH2CH2—O—C(=O)—Et  \<S\> | | Rf: 0,29 (2:1) |
| 19.27 | O | C—F | H | γ-thiobutyrolactonyl (rac) | 118–120 | |
| 19.28 | O | C—F | — | —CH2—SCH2CH—  (rac)<br>         \|<br>       COOCH3 | | Rf: 0,49 (2:1) |
| 19.29 | O | C—F | H | cyclopentyl-COOCH3  \<S\> | 119–120 | |
| 19.30 | O | C—F | H | C(CH3)2COOCH3 | 100–101 | |
| 19.31 | O | C—F | H | C(CH2)2CON(CH3)2 | 130–132 | |
| 19.32 | O | C—Cl | H | CH(CH3)—COOH (rac) | honey-like | MS: 337 (11), 302 (33), 293 (98), 265 (100). |
| 19.33 | O | C—H | H | cyclopentyl-CH2OH | 100–202 | |

TABLE 2-continued

Compounds of the formula IB:

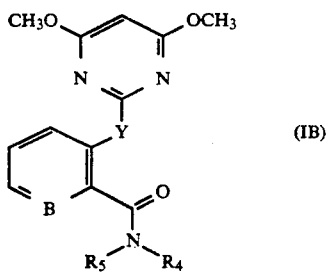

(IB)

| Ex. | Y | B | $R_5$ | $R_4$ | M.p. (°C.) | Phys. Data |
|---|---|---|---|---|---|---|
| 19.34 | O | C—H | H |  <S> | | Rf: 0,50 (EtOAc) |

TABLE 3

Compounds of the formula IC:

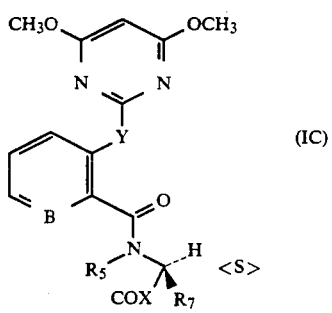

(IC)

| Ex. | Y | B | $R_5$ | $R_7$ | COX | M.p./(°C.)/Phys. Data |
|---|---|---|---|---|---|---|
| 20 | O | C—H | H | $CH_3$ | $COOCH_2CH_3$ | $^1$H-NMR: 1.32, d, J=7, $CH_3$, 4.15, q, J=7, $OCH_2$, 4.66, q, J=7, CH |
| 21 | O | C—H | H | $CH_3$ | $COOCH_3$ | $^1$H-NMR: 1.33, d, J=7, $CH_3$, 3.69, s, $COOCH_3$ 4.69, q, J=7, CH |
| 22 | O | C—H | H | i-Pr | $COOCH_3$ | liquid $R_f$ 0.41 (7:8) |
| 23 | O | C—H | H | i-Bu | $COOCH_3$ | 74–76 |
| 24 | O | C—H | H | $CH_2$-phenyl | $COOCH_3$ | liquid $R_f$ 0.35 (7:8) |
| 25 | S | C—H | H | $CH_3$ | $COOCH_3$ | solid $R_f$ 0.56 (2:1) |
| 26 | O | C—H | —$CH_2CH_2CH_2$— | | $COOC(CH_3)_3$ | liquid $R_f$ 0.42 (2:1) |
| 27 | O | N | H | $CH_3$ | $COOCH_3$ | liquid $R_f$ 0.44 (2:1) |
| 28 | O | N | H | $CH_2$-phenyl | $COOCH_3$ | liquid $R_f$ 0.66 (2:1) |
| 29 | O | N | H | i-Bu | $COOCH_3$ | 110–111 |
| 30 | O | N | H | i-Pr | $COOCH_3$ | liquid |
| 31 | O | C—H | H | $CH_3$ | $COOC(CH_3)_3$ | liquid $R_f$ 0.24 (1:2) |
| 32 | O | C—H | H | i-Bu | $COOC(CH_3)_3$ | liquid $R_f$ 0.71 (2:1) |
| 33 | O | C—H | H | $CH_2$-phenyl | $COOC(CH_3)_3$ | liquid $R_f$ 0.30 (1:2) |
| 34 | O | C—H | H | i-Bu | COOH | gum-like $R_f$ 0.17 (EtOAc) |

TABLE 3-continued

Compounds of the formula IC:

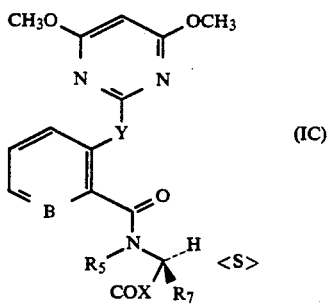

| Ex. | Y | B | R₅ | R₇ | COX | M.p/(°C.)/Phys. Data |
|---|---|---|---|---|---|---|
| 35 | O | C—H | H | CH₂–C₆H₅ | COOH | gum-like Rf: 0.45 (EtOAc/MeOH 3:1) |
| 36 | O | C—H | H | CH(CH₃)₂ | COOC(CH₃)₃ | Rf: 0,60 (2:1) |
| 37 | O | C—H | H | CH(CH₃)₂ | COOH | Rf: 0,25 (EtOAc/MeOH 3:1) |
| 38 | O | C—H | H | CH₂CH(CH₃)₂ | CONH₂ | M.p.: 131–133° C. |
| 39 | O | C—H | H | CH₂CH₂C(O)O–Et | COOCH₂CH₃ | Rf: 0,53 (2:1) |
| 40 | O | C—H | H | CH₂CH₂C(O)O–allyl | COOCH₂CH=CH₂ | Rf: 0,58 (2:1) |
| 41 | O | C—H | H | CH₂CH(CH₃)₂ | COOCH₂–C₆H₅ | Rf: 0,63 (2:1) |
| 42 | O | C—H | H | CH₂CH₂SCH₃ | COOCH₃ | Rf: 0,59 (2:1) |
| 43 | O | C—H | H | CH₂CH₃ | COOCH₃ | Rf: 0,48 (2:1) |
| 44 | O | C—H | H | CH₂-(indol-3-yl) | COOCH₃ | M.p.: 115–116° C. |
| 45 | O | C—H | H | CH₂-(imidazol-4-yl) | COOCH₃ | Rf: 0,26 (EtOAc/MeOH 9:1) |
| 46 | O | C—H | H | CH₂-(4-OH-C₆H₄) | COOCH₃ | Rf: 0,39 (2:1) |
| 47 | O | C—H | H | CH(CH₃)CH₂CH₃ | COOCH₂CH=CH₂ | Rf: 0,60 (2:1) |
| 48 | O | C—H | H | CH₂OH | COOCH₃ | Rf: 0,21 (2:1) |
| 49 | O | C—H | H | CH₂C(O)O–allyl | COOCH₂=CH₂ | Rf: 0,61 (2:1) |
| 50 | O | C—H | H | CH(CH₃)CH₂CH₃ | COOC(CH₃)₂ | Rf: 0,73 (2:1) |
| 51 | O | C—H | H | CH(CH₃)CH₂CH₃ | COOH | Rf: 0,17 (EtOAc/MeOH 3:1) |

TABLE 3-continued

Compounds of the formula IC:

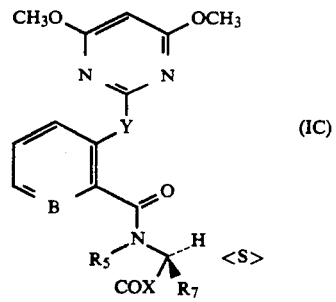

(IC)

| Ex. | Y | B | R$_5$ | R$_7$ | COX | M.p/(°C.)/Phys. Data |
|---|---|---|---|---|---|---|
| 52 | O | C—H | H | CH$_3$ | -C(=O)-NH- (tetrahydrothiophenone) (rac) | Rf: 0,51 (EtOAc) |
| 53 | O | C—H | H | CH$_2$CH(CH$_3$)$_2$ | -CNH-...-NH$_2$ (rac) | Rf: 0,33 (EtOAc) |
| 54 | O | N | H | CH$_3$ | COOH | Rf: 0,13 (EtOAc/MeOH 3:1) |
| 55 | O | N | H | CH(CH$_3$)CH$_2$CH$_3$ | COOH | Rf: 0,06 (EtOAc/MeOH 3:1) |
| 56 | O | N | H | CH$_2$CH(CH$_3$)$_2$ | COOC(CH$_3$)$_3$ | Rf: 0,48 (2:1) |
| 57 | O | N | —CH$_2$CH$_2$CH$_2$— | | COOH | Rf: 0,06 (EtOAc/MeOH 3:1) |
| 58 | O | C—H | —CH$_2$SCH$_2$— | | COOCH$_3$ | solid |
| 59 | O | C—H | —CH$_2$—CH(OH)—CH$_2$— | | COOCH$_2$CH$_3$ | Rf: 0,35 (EtOAc) |
| 60 | O | N | H | CH(CH$_3$)$_2$ | COOH | M.p.: 135–137° C. |
| 61 | O | N | H | CH$_2$CH(CH$_3$)$_2$ | COOH | M.p.: 126–128° C. |
| 62 | O | N | H | CH$_2$CH$_2$SCH$_3$ | COOCH$_3$ | Rf: 0,30 (2:1) |
| 63 | O | C—H | —CH$_2$CH$_2$CH$_2$— | | COOH | Rf: 0,10 (EtOAc/MeOH 3:1) |
| 64 | O | N | —CH$_2$CH$_2$CH$_2$— | | COOC(CH$_3$)$_3$ | Rf: 0,17 (2:1) |
| 65 | O | N | H | CH$_2$CH(CH$_3$)$_2$ | CONH$_2$ | M.p.: 136–137° C. |
| 66 | O | C—H | H | CH$_2$CH(CH$_3$)$_2$ | CONHCH(CH$_3$)$_2$ | Rf: 0,36 (2:1) |
| 67 | O | C—H | H | CH$_2$CH(CH$_3$)$_2$ | CONHCH$_2$CH$_3$ | M.p.: 120–121° C. |
| 68 | O | C—H | H | CH(CH$_3$)$_2$ | CONHCH$_2$CH$_3$ | M.p.: 126–128° C. |
| 69 | O | C—H | H | CH(CH$_3$)$_2$ | CONHCH(CH$_3$)$_2$ | M.p.: 134–136° C. |
| 70 | O | C—H | H | CH(CH$_3$)$_2$ | CONHOCH$_3$ | M.p.: 147–148° C. |
| 71 | O | N | H | CH$_3$ | COOC(CH$_3$)$_3$ | liquid |
| 72 | O | C—H | H | CH(CH$_3$)CH$_2$CH$_3$ | CONHCH$_2$CH$_3$ | M.p.: 151–152° C. |
| 73 | O | C—H | H | CH(CH$_3$)CH$_2$CH$_3$ | CONHC(CH$_3$)$_3$ | Rf: 0,68 (EtOAc) |
| 74 | O | C—H | H | CH(CH$_3$)CH$_2$CH$_3$ | (acetamido-OH derivative) <S> | Rf: 0,33 (EtOAc) |
| 75 | O | N | H | CH$_2$CH$_2$COOCH$_2$CH$_3$ | COOCH$_2$CH$_3$ | Rf: 0,39 (2:1) |
| 76 | O | N | H | CH(CH$_3$)CH$_2$CH$_3$ | COOCH$_3$ | Rf: 0,34 (2:1) |
| 77 | O | C—H | H | CH$_3$ | CONH$_2$ | M.p.: 129–131° C. |
| 78 | O | C—H | H | CH(CH$_3$)$_2$ | CONH$_2$ | M.p.: 138–139° C. |
| 79 | O | C—H | —CH$_2$CH$_2$CH$_2$— | | CONH$_2$ | Rf: 0,06 (EtOAc) |
| 80 | O | C—H | H | CH$_3$ | CONHCH$_2$CH$_3$ | Rf: 0,40 (EtOAc) |
| 81 | O | C—H | H | CH$_3$ | CONHCH(CH$_3$)$_2$ | M.p.: 113–115° C. |
| 82 | O | C—H | H | CH$_3$ | CON(CH$_3$)$_2$ | Rf: 0,20 (EtOAc) |
| 83 | O | C—H | H | CH$_3$ | (acetamido-C≡N derivative) | M.p.: 179–180° C. |
| 84 | O | C—F | H | CH$_3$ | COOH | $[\alpha]_D$ = +5,25° C. |
| 85 | O | C—F | H | CH$_3$ | COOC(CH$_3$)$_3$ | $[\alpha]_D$ = −13,1° C. |
| 86 | S | C—H | H | CH$_3$ | COOC(CH$_3$)$_3$ | M.p.: 118–119° C. |
| 87 | S | C—H | H | CH$_3$ | CONH$_2$ | M.p.: 159–161° C. |
| 88 | S | C—H | H | CH$_3$ | COOH | M.p.: 136–138° C. |

5,262,386

TABLE 3-continued

Compounds of the formula IC:

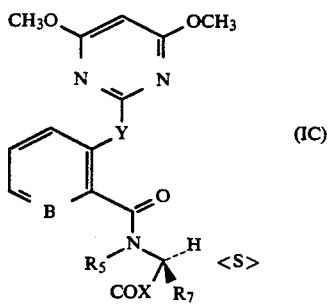

| Ex. | Y | B | R5 | R7 | COX | M.p/(°C.)/Phys. Data |
|---|---|---|---|---|---|---|
| 89 | O | C—Cl | H | CH3 | COOC(CH3)3 | [α]D = −14,14° C. |
| 90 | S | C—F | H | CH3 | COOH | Rf: 0,13 (EtOAc/MeOH 3:1) |
| 91 | S | C—F | H | CH3 | COOC(CH3)3 | Rf: 0,45 (7:8) |
| 92 | S | C—F | —CH2CH2CH2— | | COOC(CH3)3 | Rf: 0,60 (2:1) |
| 93 | O | C—H | H | CH2CH3 | COOC(CH3)3 | Rf: 0,60 (2:1) |
| 94 | O | C—H | H | CH2CH3 | COOH | Rf: 0,08 (EtOAc/MeOH 3:1) |
| 95 | O | C—H | H | CH2SSC(CH3)3 | COOCH3 | Rf: 0,57 (2:1) |
| 96 | O | C—H | H | Phenyl | COOCH3 | Rf: 0,55 (1:2) |
| 97 | O | C—H | H | CH2CH3 | CONHCH2CH3 | Rf: 0,21 (2:1) |
| 98 | O | C—H | H | CH2CH3 | CON(CH3)2 | Rf: 0,42 (EtOAc) |
| 99 | O | C—H | H | CH2CH3 | CON(CH3)2 | Rf: 0,57 (EtOAc) |
| 100 | O | C—H | H | CH2CH3 | CONH2 | Rf: 0,33 (EtOAc) |
| 101 | O | C—H | —CH2CH2— | | COOCH3 | Rf: 0,48 (EtOAc) |
| 102 | S | C—CH3 | H | CH3 | COOC(CH3)3 | Rf: 0,34 (7:8) |
| 103 | S | C—CH3 | H | CH3 | COOH | Rf: 0,18 (EtOAc/MeOH 3:1) |
| 104 | S | C—H | H | CH2CH=CH2 | COOCH3 | Rf: 0,29 (7:8) |
| 105 | S | C—F | —CH2CH2CH2— | | COOH | Rf: 0,13 (EtOAc/MeOH 3:1) |
| 106 | O | C—F | —CH2CH2CH2— | | COOH | Rf: 0,08 (EtOAc/MeOH 3:1) |
| 107 | O | C—F | —CH2CH2CH2— | | COOC(CH3)3 | Rf: 0,45 (2:1) |
| 108 | O | C—F | H | CH2CH2COOCH2CH3 | COOCH2CH3 | Rf: 0,56 (2:1) |
| 109 | O | C—F | H | CH—SSC(CH3)3 | COOCH3 | Rf: 0,60 (2:1) |
| 110 | O | C—F | H | CH(CH3)2 | COOC(CH3)3 | Rf: 0,38 (7:8) |
| 111 | O | C—F | H | CH2CH3 | COOC(CH3)3 | Rf: 0,36 (7:8) |
| 112 | O | C—F | H | CH(CH3)2 | COOH | Rf: 0,18 (EtOAc/MeOH 3:1) |
| 113 | O | C—F | H | CH(CH3)2 | COOC(CH3)3 | Rf: 0,38 (7:8) |
| 114 | O | C—F | H | CH2CH3 | COOC(CH3)3 | Rf: 0,36 (7:8) |
| 115 | O | C—F | H | CH(CH3)2 | COOH | Rf: 0,18 (EtOAc/MeOH 3:1) |
| 116 | O | C—F | H | CH2CH3 | COOH | Rf: 0,08 (EtOAc/MeOH 3:1) |
| 117 | O | C—OCH3 | H | CH3 | COOC(CH3)3 | Rf: 0,36 (2:1) |
| 118 | O | C—OCH3 | H | CH3 | COOH | Rf: 0,08 (EtOAc/MeOH 3:1) |
| 119 | O | C—OCH3 | —CH2CH2CH2— | | COOC(CH3)3 | M.p.: 64–66° C. |
| 120 | O | C—CH3 | H | CH3 | COOCH2CH3 | Rf: 0,38 (2:1) |
| 121 | O | N | H | CH(CH3)2 | COOC(CH3)3 | Rf: 0,46 (2:1) |
| 122 | O | N | —CH2CH2CH2— | | COOC(CH3)3 | M.p.: 129–131° C. |
| 123 | O | N | —CH2CH2CH2—<br>\|<br>OH | | COOC(CH3)3 | Rf: 0,18 (EtOAc) |
| 124 | O | C—H | H | CH2CH(CH3)3 | CONH-CH(CH3)-CH2OH <S> | Rf: 0,25 (EtOAc) |
| 125 | O | C—H | H | CH(CH3)2 | CONH-CH(CH3)-CH2OH <S> | Rf: 0,29 (EtOAc) |
| 126 | O | C—H | H | CH(CH3)CH2CH3 | CONHCH(CH3)2 | Mp.: 131–133° C. |
| 127 | O | C—H | H | C(CH3)3 | COOCH3 | Rf: 0,58 (1:2) |

TABLE 4

Compounds of the Formula

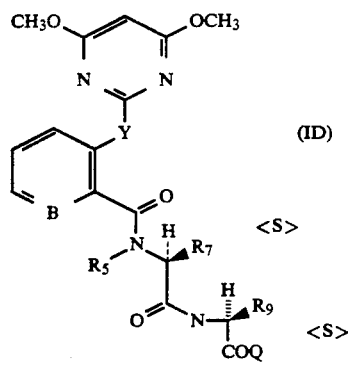

(ID)

| Ex. | B | Y | R5 | R7 | R9 | COQ | Phys. Data |
|---|---|---|---|---|---|---|---|
| 128 | C—H | O | H | H | CH3 | COOCH2CH3 | Rf: 0,48 (2:1) |
| 129 | C—H | O | H | i-Pr | CH3 | COOCH2CH3 | Rf: 0,33 (2:1) |
| 130 | C—H | O | H | CH3 | CH3 | COOCH2CH3 | Rf: 0,25 (2:1) |
| 131 | C—H | O | H | s-Bu | CH3 | COOCH2CH3 | Rf: 0,45 (2:1) |
| 132 | C—H | O | H | CH2CH3 | H | COOC(CH3)3 | Rf: 0,40 (2:1) |
| 133 | C—H | O | H | CH3 | H | COOC(CH3)3 | Rf: 0,37 (2:1) |
| 134 | C—H | O | H | CH3 | H | COOH | Rf: 0,05 (EtOAc/MeOH 3:1) |
| 135 | C—H | O | H | CH2CH3 | CH3 | COOCH2CH3 | Rf: 0,58 (EtOAc) |
| 136 | C—H | O | H | CH2CH3 | H | COOH | Rf: 0,05 (EtOAc/MeOH 3:1) |
| 137 | C—H | O | H | H | H | COOC(CH3)3 | Rf: 0,23 (2:1) |
| 138 | C—H | O | H | H | H | COOH | Rf: 0,03 (EtOAc/MeOH 3:1) |
| 139 | C—H | O | H | H | CH3 | COOC(CH3)3 | Rf: 0,34 (2:1) |
| 140 | C—H | O | H | H | CH3 | COOH | Rf: 0,08 (AtOAc/MeOH 3:1) |
| 141 | C—H | O | H | CH3 | CH3 | COOC(CH3)3 | Rf: 0,36 (2:1) |
| 142 | C—H | O | H | CH3 | CH3 | COOH | Rf: 0,08 (AtOAc/MeOH 3:1) |
| 143 | C—H | O | H | i-Pr | CH3 | COOC(CH3)3 | Rf: 0,50 (2:1) |
| 144 | C—H | O | H | i-Pr | CH3 | COOH | Rf: 0,10 (2:1) |
| 145 | C—H | O | H | CH3 | CH3 | ![structure] | Rf: 0,37 (EtOAc) |

TABLE 5

Compounds of the Formula

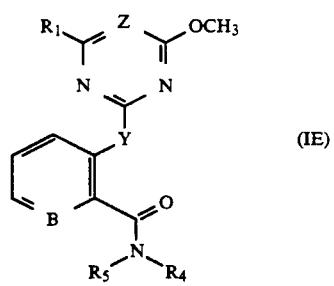

(IE)

| Ex. | B | Y | Z | R1 | R5 | R4 | Phys. Data |
|---|---|---|---|---|---|---|---|
| 146 | C—H | O | C—H | CH3 | H | ethyl lactate <S> | Rf: 0,047 (2:1) |
| 147 | C—H | O | N | OCH3 | H | ethyl lactate <S> | Rf: 0,60 (2:1) |

TABLE 5-continued

Compounds of the Formula

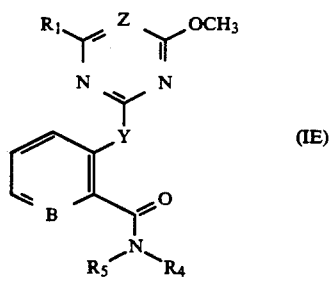

(IE)

| Ex. | B | Y | Z | R₁ | R₅ | R₄ | Phys. Data |
|---|---|---|---|---|---|---|---|
| 148 | C—H | O | N | OCH₃ | H | (tetrahydrothiophen-3-yl methyl, rac) | Rf: 0,38 (2:1) |
| 149 | C—H | O | N | OCH₃ | H | (tert-butyl propanoate, <S>) | Rf: 0,24 (7:8) |
| 150 | C—H | O | N | OCH₃ | H | (propanoic acid, <S>) | Rf: 0,16 (EtOAc/MeOH 3:1) |

C. FORMULATION EXAMPLES

EXAMPLE F1

To prepare a 25% wettable powder, the components listed below are mixed with one another:

| | Percent by weight |
|---|---|
| Compound of the formula I according to table 2-5 | 25 |
| Hydrated silica (carrier, grinding auxiliary) | 20 |
| Sodium lauryl sulfate (wetting agent) | 2 |
| Sodium lignosulfonate (dispersant) | 4 |
| Kaolin (carrier) | 49 |
| | 100 |

First, the liquid, or molten, active substance is applied to the initially introduced silica in a grinding device, the other components are then admixed. Using a pinned-disc mill or a comparable grinding device, the mixture is ground finely.

When stirred into water, the resulting wettable powder gives a fine suspension which is suitable as a ready-to-use spray liquor.

Active substances which are particularly suitable for this formulation are compounds of the formula I which are liquid or have a low melting point, i.e. up to about +100° C.

EXAMPLE F2

Compounds of the formula I which have a high melting point, i.e. above about +100° C., can preferably be used as active substances in concentrated wettable powders, for example as follows:

| | Percent by weight |
|---|---|
| Compound of the formula I according to table 2-5 | 75 |
| Hydrated silica (carrier, grinding auxiliary) | 1 |
| Alkylnaphthalenesulfonate and alkylcarboxylate sulfate as sodium salts, for example "Morowett EFW" (trade name of De Soto) (wetting agent) | 2 |
| Sulfonated naphthalene/formaldehyde condensate as the sodium salt, for example "Morowett D-425"(trade name of De Soto) (dispersant) | 10 |
| Polyvinylpyrrolidone, for example PVP-K-30 (GAF Corp.) (binder) | 1 |
| Kaolin (carrier) | 11 |
| | 100 |

The components are mixed with one another and ground finely using a pinned-disc mill or a comparable grinding device, in particular a fluid energy mill.

When stirred into water, the resulting wettable powder gives a fine suspension of any desired concentration which is suitable as a ready-to-use spray liquor.

EXAMPLE F3

A wettable powder on the basis of the composition of Example F1 can also be converted into dispersible granules. For this purpose, the ground powder is sprayed with an aqueous solution of the binder in a suitable granulation device (for example granulating plate, mixing drum, high-speed mixer or fluidised bed granulator) until agglomerations have formed. The water which has been added is subsequently removed in a drying process. The granules of the desired size are separated by sieving.

Compared with the wettable powder, the resulting granules have various advantages (no dust formation on application, more easy metering due to better flow properties). After the preparation has been stirred into water and the granules have disintegrated completely into the primary particles, the application is just the same as in the case of the wettable powder.

EXAMPLE F4

In the customary organic solvents, the compounds of the formula I have limited solubility. Accordingly, emulsifiable concentrates of a relatively low concentration are possible, for example:

| | |
|---|---|
| Compound of the formula I according to table 2-5 | 125 g/l |
| "Sorprophor BSU" (trade name of Rhone-Poulenc) (emulsifier) | 300 g/l |
| N-Methyl-2-pyrrolidone (solvent) | to 1000 ml |

The active substance and the emulsifier are introduced into the solvent with stirring. The mixture is stirred until a homogeneous solution has formed.

The resulting emulsifiable concentrate can be emulsified in water, giving a ready-to-use spray liquor of the desired concentration.

EXAMPLE F5

Compounds of the formula I which have a melting point above about +60° C. can also be formulated as so-called suspension concentrates ("flowables"); for example:

| | |
|---|---|
| Compound of the formula I according to table 2-5 | 250 g/l |
| Ethylene glycol (antifreeze) | 80 g/l |
| Silica (settling inhibitor) | 5 g/l |
| Xanthane gum, for example "Kelzan" (trade name of Kelco) (thickener) | 2 g/l |
| Silicone defoamer, for example "Rhodorsil 426" (trade name of Rhone-Poulenc) | 5 g/l |
| Nonylphenol polyethoxylate (wetting agent) | 20 g/l |
| Sulfonated naphthalene/formaldehyde condensate as the sodium salt, for example "Morowett D-425"(trade name of De Soto)(dispersant) | 40 g/l |
| Water | to 1000 ml |

The formulation auxiliaries are dissolved in water. The previously ground active substance is dispersed in the solution with stirring. The resulting coarse suspension is now subjected to wet grinding (for example in a colloid mill or a ball mill with stirring device). If desired, small amounts of further additives are now possible, such as antifoams, settling inhibitors and biocides.

For use, the resulting "flowables" can be diluted with water in any desired ratio, giving a ready-to-use spray liquor of the desired concentration.

BIOLOGICAL EXAMPLES

EXAMPLE B1

Preemergence herbicidal action

In a greenhouse, immediately after the test plants have been sown in seed trays, the surface of the soil is treated with an aqueous spray mixture in an amount corresponding to a rate of application of 3 kg of test compound/hectare. The seed trays are kept in the greenhouse at 22°-25° C. and 50-70% relative humidity.

After 3 weeks, the herbicidal action is evaluated according to a scale of three ratings (2=80-100% damage, 1=30-79% damage, 0=0-30% damage) in comparison with an untreated control group.

The compounds of formula I according to the tables 2-5 exhibit pronounced herbicidal activity in this test.

Examples for the good preemergence herbicidal activity of the compounds of the formula I are given in Table B1:

TABLE B1

| Compound according to example: | Preemergence herbicidal action Weed: | | | | |
|---|---|---|---|---|---|
| | Sorghum | Echinochloa | Avena | Alopecurus | Chenopodium |
| 3 | 2 | 2 | 2 | 2 | 2 |
| 5 | 2 | 2 | 2 | 2 | 2 |
| 9 | 2 | 2 | 2 | 2 | 2 |
| 10 | 2 | 2 | 2 | 2 | 2 |
| 11 | 2 | 2 | 2 | 2 | 2 |
| 12 | 2 | 2 | 2 | 2 | 2 |
| 18 | 2 | 2 | 2 | 2 | 2 |
| 20 | 2 | 2 | 2 | 2 | 2 |
| 22 | 2 | 2 | 2 | 2 | 2 |
| 27 | 2 | 2 | 2 | 2 | 2 |
| 28 | 2 | 2 | 2 | 2 | 2 |
| 29 | 2 | 2 | 2 | 2 | 2 |
| 30 | 2 | 2 | 2 | 2 | 2 |
| 31 | 2 | 2 | 2 | 2 | 2 |

EXAMPLE B2

Postemergence herbicidal action (contact herbicide)

A number of weeds, both mono- and dicotyledonous, are sprayed postemergence (in the 4-to 6-leaf stage) with an aqueous active ingredient dispersion at a rate of 3 kg of test compound per hectare and kept at 24°-26° C. and 45-60% relative humidity. The test is evaluated 15 days after the treatment. In this test too, the compounds of formula I according to the tables 2-5 exhibit good herbicidal activity.

EXAMPLE B3

Herbicidal action in wild rice (paddy rice)

The weed Echinochloa crus galli, which occur in water, is sown in plastic beakers (surface: 60 cm$^2$; volume: 500 ml). After sowing, the beakers are filled with water up to the surface of the soil. 3 days after sowing, the water level is increased to slightly above the soil surface (3-5 mm). Application is effected 3 days after sowing by spraying the beakers with the test compounds. The rate of application corresponds to a concentration of 3 kg of active ingredient per hectare. The beakers are then kept in the greenhouse under optimum growth conditions for rice weeds, i.e. at 25°-30° C. and at high humidity.

The evaluation of the tests takes place 3 weeks after application. The compounds of formula I according to the tables 2-5 damage the weeds but not the rice.

EXAMPLE B4

Growth inhibition of tropical cover crops

The test plants Centrosema pubescens and Psophocarpus palustris are propagated by means of cuttings in 4 cm peat pots containing earth (45%), peat (45%) and Zonolite (10%). The cuttings are raised in a greenhouse at a day temperature of 27° C. and a night temperature of 23° C. The plants are illuminated for at least 14 hours/day with an intensity of at least 7000 lux.

About 50 days after the cuttings were taken, they are transplanted into 13 cm pots, 4-5 plants/pot. After a further 60 days, the plants are cut back to a height of about 15 cm and treated by spraying with an aqueous spray mixture at a concentration of 0.1 to 300 g of active ingredient/ha (usually as a 25% formulation). The amount of water applied is about 200 l/ha.

4 weeks after application, the weight of the new growth is determined and expressed as a percentage of the average of the untreated controls. The necrotic damage is given as a percentage of the total leaf area.

The new growth on the treated plants is markedly less than that on the untreated controls.

EXAMPLE B5

Growth regulation of soybeans

Test plants of the Williams variety are sown in 11 cm clay pots containing earth (45%), peat (45%) and Zonolite (10%) and are raised in a climatic chamber at a day temperature of 24° C. and a night temperature of 19° C. The plants are illuminated for 16 hours per day with an intensity of about 350 micro-einsteins.

About 24 days after sowing, the plants are transplanted into 18 cm pots, 2 plants/pot. After a further 12 days, when the plants are in the 5-6 trefoil leaf stage, the test compound is applied at a concentration of 0.1 to 300 g of active ingredient/ha, usually as a 25% formulation and in an aqueous spray mixture. The amount of water applied is about 200 l/ha.

Evaluation is made about 4 weeks after application. The height of the new growth is measured and expressed as a percentage of the average of the untreated controls. The necrotic damage is given as a percentage of the total leaf area.

The treated plants exhibit markedly less new growth than do the untreated controls.

EXAMPLE B6

Growth inhibition of cereals

Test plants (summer barley of the Iban variety) are sown in 15 cm plastic pots containing sterile earth and raised in a climatic chamber at a day temperature of 10°-15° C. and a night temperature of 5°-10° C. The plants are illuminated for 13.5 hours per day with an intensity of about 25000 lux.

About 34 days after sowing, and after the plants have been thinned out to 4 plants/pot, the test compound is applied at a concentration of 0.1 to 300 g of active ingredient/ha, usually as a 25% formulation and in an aqueous spray mixture. The amount of water applied is about 500 l/ha. After application, the plants are placed in a greenhouse at a day temperature of at least 10° C. They are illuminated for at least 13.5 hours/day.

Evaluation is made about 28 days after the treatment. The height of the new growth is expressed as a percentage of the average of the untreated controls. The necrotic damage is given as a percentage of the total leaf area.

The treated plants exhibit a reduction in new growth in comparison with untreated controls.

EXAMPLE B7

Growth inhibition of grasses

A mixture of grasses (e.g. Poa, Festuca, Lolium, Bromus, Cynosurus) and clover (Trifolium pratense/-repens) is sown in 15 cm plastic pots containing sterile earth and the plants are raised in a greenhouse at a day temperature of 21° C. and a night temperature of 17° C. The plants are illuminated for 13.5 hours/day with an intensity of at least 7000 lux. The emergent plants are cut back weekly to a height of about 6 cm. About 42 days after sowing and 1 day after the last cut, the test compound is applied at a concentration of 0.1 to 300 g of active ingredient/ha, usually as a 25% formulation and in an aqueous spray mixture. The amount of water applied is about 500 l/ha.

Evaluation is made about 3 weeks after treatment. The height of the new growth is measured and expressed as a percentage of the average of the untreated controls. The necrotic damage is given as a percentage of the total leaf area.

The tested compounds of formula I according to the tables 2-5 effect a reduction in new growth in comparison with untreated controls.

What is claimed is:

1. A pyrimidinyl-salicylamide of the formula I

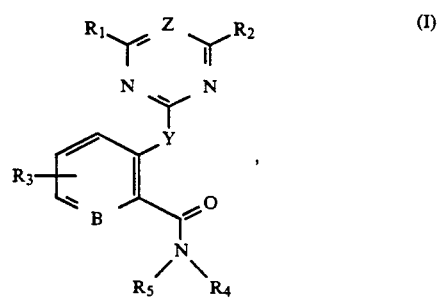

in which B is nitrogen, methine, or fluorine-, chlorine-, methyl-, methoxy-, 2-propenyloxy-, 2-propynyloxy-, difluoromethoxy-, phenoxy-, methylthio-, phenylthio-, phenyl- or benzyloxy-substituted methine; Y is oxygen or sulfur; Z is methine; $R_1$ is chlorine, methyl, methoxy, ethoxy, difluoromethoxy, methylamino, ethylamino or dimethylamino; $R_2$ is methyl, methoxy or difluoromethoxy; $R_3$ is hydrogen, fluorine, chlorine, methyl or methoxy; $R_4$ is one of the groups (a), (b) or (c)

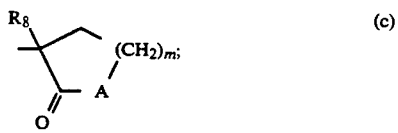

$R_5$ is hydrogen, methyl, or together with $R_7$ is —(CH$_2$)$_p$—, —CH$_2$SCH$_2$— or —CH$_2$CHOHCH$_2$—; $R_6$ is hydroxymethyl, formyl, cyano, $C_{1-4}$-alkoxyimino, hydroxyimino, phosphono, phosphino, methylphosphino or a group COX; $R_7$ is hydrogen; $C_{1-4}$alkyl which is unsubstituted or substituted by hydroxyl, $C_{1-4}$alkoxy, mercapto, acylmercapto, $C_{1-4}$-alkylthio, vinyl, phenyl, 4-hydroxyphenyl, 4-imidazolyl, 3-indolyl, hydroxycarbonyl, $C_{1-4}$alkoxycarbonyl, 2-propenyloxycarbonyl, cyano, carbamoyl; trifluoromethyl; ethynyl; vinyl which is unsubstituted or substituted by chlorine or methoxy; or phenyl which is unsubstituted or substituted by fluorine, chlorine, methyl, trifluoromethyl or methoxy; or cyano or $C_{1-4}$-alkoxycarbonyl; $R_8$ is hydrogen or methyl; A is oxygen, sulfur or —NH—; m is 1, 2 or 3; n is 0, 1, 2 or 3; p is 2 or 3; X is hydroxyl, $C_{1-4}$alkoxy, $C_{3-4}$alkenyloxy, mercapto, $C_{1-4}$alkylthio, amino, $C_{1-4}$alkylamino, $C_{2-4}$dialkylamino, or $C_{1-4}$-alkoxy, $C_{3-4}$-alkenyloxy, mercapto, $C_{1-4}$-alkylthio, amino, $C_{1-4}$-alkylamino, $C_{2-4}$dialkylamino, $C_{1-4}$-alkoxyamino substituted by phenyl, benzyloxy or $C_{1-2}$-alkoxy, or a further one of the groups (d) and (e)

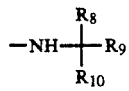 (d)

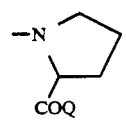 (e)

$R_9$ is hydrogen, $C_{1-4}$alkyl or benzyl; $R_{10}$ is hydroxymethyl, cyano or a group COQ'; Q is hydroxyl, $C_{1-4}$alkoxy, 2-propenyloxy, benzyloxy, amino or a group (d); Q' is hydroxyl, $C_{1-4}$alkoxy, 2-propenyloxy, benzyloxy, amino or a group (d), and the salts of those compounds of the formula I which have a free hydroxycarbonyl group.

2. A compound of the formula I according to claim 1, in which B is nitrogen, methine, or fluorine-, chlorine-, methyl-, methoxy-, 2-propenyloxy-, 2-propynyloxy-, difluoromethoxy- or benzyloxy-substituted methine; Y is oxygen or sulfur; Z is methine or nitrogen; $R_1$ is chlorine, methyl, methoxy, ethoxy, difluoromethoxy, methylamino, ethylamino or dimethylamino; $R_2$ is methyl, methoxy or difluoromethoxy; $R_3$ is hydrogen, fluorine, chlorine, methyl or methoxy; $R_4$ is one of the groups (a), (b) or (c)

 (a)

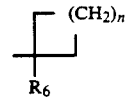 (b)

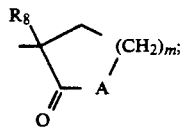 (c)

$R_5$ is hydrogen, methyl, or together with $R_7$ is —(CH$_2$)$_p$— or —CH$_2$CHOHCH$_2$—; $R_6$ is hydroxymethyl, cyano, phosphono, phosphino, methylphosphino or a group COX; $R_7$ is hydrogen; $C_{1-4}$alkyl which is unsubstituted or substituted by hydroxyl, $C_{1-4}$alkoxy, mercapto, acylmercapto, $C_{1-4}$alkylthio, phenyl, 4-hydroxyphenyl, 4-imidazolyl, 3-indolyl, hydroxycarbonyl, $C_{1-4}$alkoxycarbonyl, 2-propenyloxycarbonyl, cyano, carbamoyl, methylphosphino or methylsulfoximino; trifluoromethyl; ethynyl; vinyl which is unsubstituted or substituted by chlorine or methoxy; or phenyl which is unsubstituted or substituted by fluorine, chlorine, methyl, trifluoromethyl or methoxy; $R_8$ is hydrogen or methyl; A is oxygen, sulfur or —NH—; m is 1, 2 or 3; n is 0, 1, 2 or 3; p is 2 or 3; X is hydroxyl, $C_{1-4}$alkoxy, $C_{3-4}$alkenyloxy, benzyloxy, mercapto, $C_{1-4}$alkylthio, amino, $C_{1-4}$alkylamino, $C_{2-4}$dialkylamino, or a further one of the groups (d) and (e)

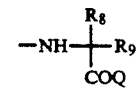 (d)

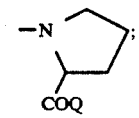 (e)

$R_9$ is hydrogen, $C_{1-4}$alkyl or benzyl; $R_{10}$ is COQ'; Q is hydroxyl, $C_{1-4}$alkoxy, 2-propenyloxy, benzyloxy or amino; Q' is hydroxyl, $C_{1-4}$alkoxy, 2-propenyloxy, benzyloxy or amino; and the salts of compounds of the formula I which have a free hydroxycarbonyl group.

3. A compound of the formula I according to claim 1, in which B is methine or nitrogen.

4. A compound of the formula I according to claim 3, in which methine is substituted by fluorine or chlorine.

5. A compound of the formula I as claimed in claim 1, in which Y is oxygen.

6. A compound of the formula I according to claim 1, in which $R_3$ is hydrogen.

7. A compound of the formula I according to claim 1, in which $R_4$ is a group (a).

8. A compound of the formula I according to claim 1, in which $R_5$ is hydrogen.

9. A compound of the formula I according to claim 1, in which $R_6$ is cyano or a COX group.

10. A compound of the formula I according to claim 7, in which X is $C_{1-4}$alkoxy or amino.

11. A compound of the formula I according to claim 1, in which $R_7$ is hydrogen, $C_{1-4}$alkyl, 2-propenyl or together with $R_5$ is —CH$_2$CH$_2$CH$_2$— or —CH$_2$SCH$_2$—.

12. A compound of the formula I according to claim 1, in which $R_8$ is hydrogen.

13. A compound of the formula I according to claim 1, in which $R_4$ is a chiral group of the formula IA

 (IA)

with <S> chirality.

14. A compound of the formula I according to claim 1, in which $R_4$ is the group (c) in which A is oxygen or sulfur and m is 1.

15. A compound of the formula I according to claim 12, in which $R_4$ is a group of the formula IF

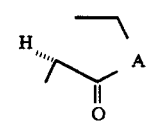 (IF)

with <S> chirality.

16. A compound of the formula I according to claim 1, in which $R^1$ is chlorine, methyl, methoxy, ethoxy, difluoromethoxy, methylamino or dimethylamino;
$R^2$ is methoxy;
$R^3$ is hydrogen;
B is nitrogen, methine or chlorine- or fluorine-substituted methine;
Y is oxygen or sulfur;
Z is methine; and in which $NR^4R^5$ is one of the groups:
Q1: 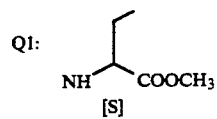
Q2: 
Q3: 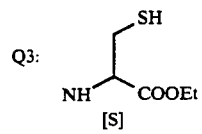
Q4: 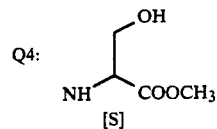
Q5: 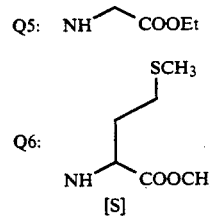
Q7: 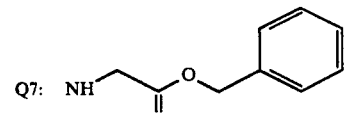
Q8: 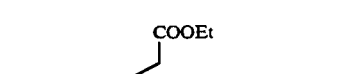
Q9: 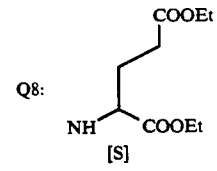
Q10: 
Q11: 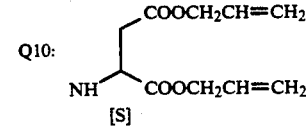
-continued
Q12: 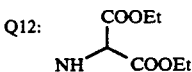
Q13: 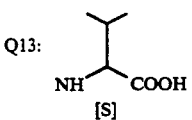
Q14: 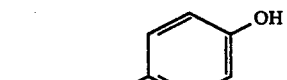
Q15: 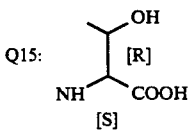
Q16: 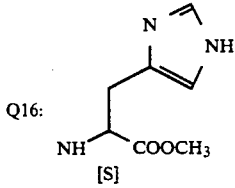
Q17: 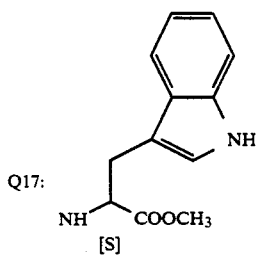
Q18: 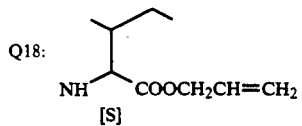
Q19: 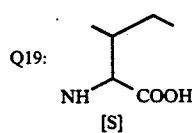
Q20: 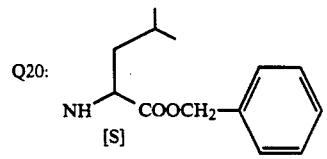
Q21: 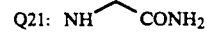

-continued
Q22: 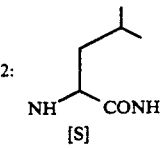
Q23: 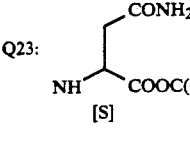
Q24: 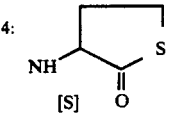
Q25: 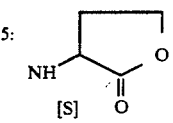
Q26: 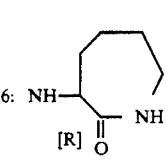
Q27: 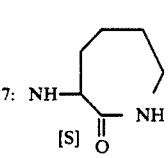
Q28: 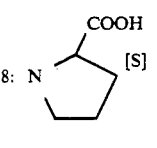
Q29: 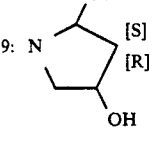
Q30: 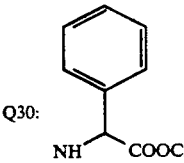
Q31: 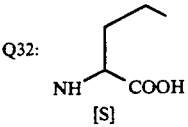
Q32: 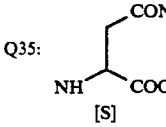
-continued
Q33: 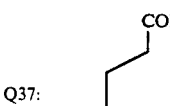
Q34: 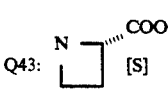
Q35: 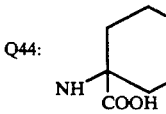
Q36: 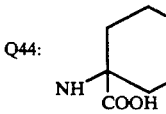
Q37: 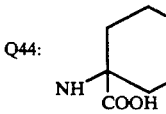
Q38:
Q39:
Q40:
Q41:
Q42:
Q43:
Q44:

-continued

Q45: 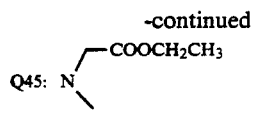

Q46: 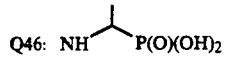

Q47: 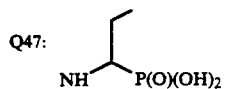

Q48: 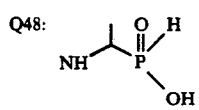

Q49: 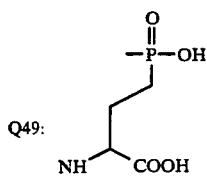

Q50: 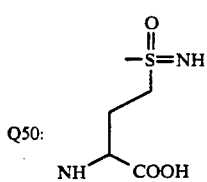

Q51: 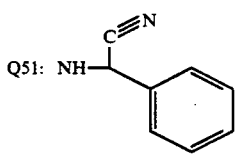

Q52: 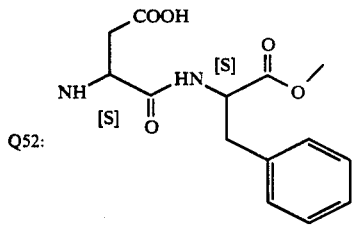

Q53: 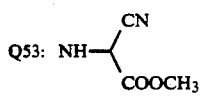

Q54: 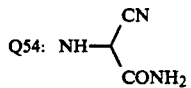

Q55: 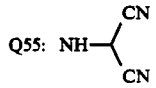

Q56: 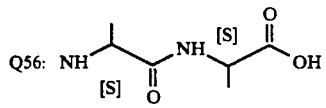

-continued

Q57: 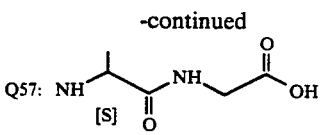

Q58: 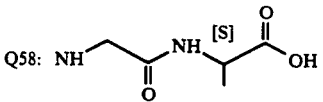

Q59: 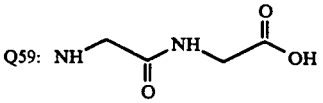

Q60: 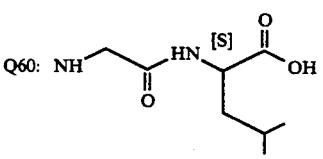

Q61: 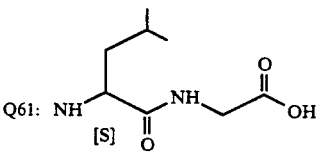

Q62: 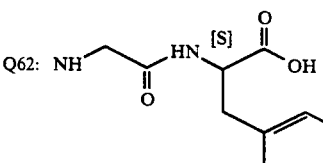

Q63: 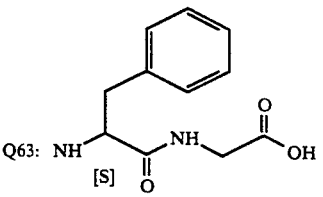 or

Q64: 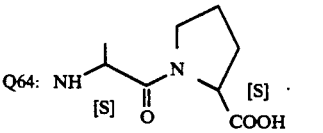

17. A compound of the formula I according to claim 1, selected from the group comprising methyl N-(o)-((4,6-dimethoxy-2-pyrimidinyl)oxy)benzoyl)glycinate;

ethyl N-(o-((4,6-dimethoxy-2-pyrimidinyl)oxy)benzoyl)-L-alaninate;

rac-o-((4,6-dimethoxy-2-pyrimidinyl)oxy)-N-(dihydro-2-oxo-3(2H)-thienyl)benzamide;

methyl N-(o-((4,6-dimethoxy-2-pyrimidinyl)oxy)benzoyl)-L-alaninate;

methyl N-(o-((4,6-dimethoxy-2-pyrimidinyl)oxy)benzoyl)-L-valinate;

methyl N-(o-((4,6-dimethoxy-2-pyrimidinyl)oxy)benzoyl)-L-leucinate;

rac-N-(1-carbamoyl-1,2-dimethylpropyl)-o-((4,6-dimethoxy-2-pyrimidinyl)thio)-benzamide;

tert-butyl 1-(o-((4,6-dimethoxy-2-pyrimidinyl)oxy)benzoyl)-L-prolinate;

methyl N-((3-((4,6-dimethoxy-2-pyrimidinyl)oxy)-2-pyridyl)carbonyl)-L-alaninate;

methyl N-((3-((4,6-dimethoxy-2-pyrimidinyl)oxy)-2-pyridyl)carbonyl)glycinate;

o-((4,6-dimethoxy-2-pyrimidinyl)oxy)-N-(<S>-1-(hydroxymethyl)-2-methylpropyl)-benzamide; and N-(1-cyano-1-methylethyl)-o-((4,6-dimethoxy-2-pyrimidinyl)oxy)benzamide.

18. A herbicidal and plant-growth-inhibiting composition, which contains at least an effective amount of a pyrimidinyl-salicylamide of the formula I, according to claim 1 and an invert carrier.

19. A composition according to claim 18, which contains between 0.001% and 95% by weight of active substance as defined in formula I according to claim 1.

20. A method of controlling undesired plant growth, which comprises applying an active substance of the formula I according to claim 1, or a composition containing this active substance, in an effective amount to the plants or their environment.

21. A method according to claim 20, wherein an amount of active substance of between 0.001 and 3 kg per hectare is applied.

22. A method of regulating plant growth, which comprises applying an active substance of the formula I according to claim 1, or a composition containing this active substance, in an effective amount to the plants or their environment.

23. A method according to claim 20 for selective pre- or post-emergence control of weeds in crops.

24. N-(o-((4,6-dimethoxy-2-pyrimidinyl)oxy)benzoyl)-L-alanine according to claim 1.

* * * * *